US008483814B2

(12) United States Patent
Zanetti et al.

(10) Patent No.: US 8,483,814 B2
(45) Date of Patent: *Jul. 9, 2013

(54) SCG POINT PICK PROCESS FOR USE WITH MULTIAXIS ACCELEROMETERS

(76) Inventors: John M. Zanetti, Arkansaw, WI (US); Douglas Perlick, Buffalo, MN (US)

( * ) Notice: Subject to any disclaimer, the term of this patent is extended or adjusted under 35 U.S.C. 154(b) by 109 days.

This patent is subject to a terminal disclaimer.

(21) Appl. No.: 12/769,970

(22) Filed: Apr. 29, 2010

(65) Prior Publication Data

US 2011/0112421 A1    May 12, 2011

Related U.S. Application Data

(63) Continuation-in-part of application No. 11/444,048, filed on May 31, 2006, now Pat. No. 7,715,909.

(60) Provisional application No. 60/687,258, filed on Jun. 3, 2005.

(51) Int. Cl.
*A61B 5/04* (2006.01)

(52) U.S. Cl.
USPC ............................ 600/523; 600/509; 600/528

(58) Field of Classification Search
USPC ................ 607/9, 17, 120; 600/508, 509, 515, 600/517, 519, 523, 528
See application file for complete search history.

(56) References Cited

U.S. PATENT DOCUMENTS

| 4,989,611 | A | * | 2/1991 | Zanetti et al. | 600/508 |
| 6,024,705 | A | * | 2/2000 | Schlager et al. | 600/508 |
| 6,978,184 | B1 | * | 12/2005 | Marcus et al. | 607/120 |

* cited by examiner

*Primary Examiner* — Christopher D Koharski
*Assistant Examiner* — Pamela M Bays
(74) *Attorney, Agent, or Firm* — Beck & Tysver PLLC (57) ABSTRACT

A seismocardiograph using multiple accelerometer sensors to identify cardiac valve opening and closing times. A methodology for selecting event times is also disclosed.

10 Claims, 6 Drawing Sheets

SCG POINT PICK PROCESS FOR USE WITH MULTIAXIS ACCELEROMETERS

CROSS REFERENCE TO RELATED CASES

The present application is a Continuation-In-Part U.S. patent application Ser. No. 11/444,048 filed May 31, 2006, now U.S. Pat. No. 7,715,909, which in turn incorporates by reference and claims the benefit of U.S. Provisional Application 60/687,258 filed Jun. 3, 2005 and entitled SCG Point Pick Process and Method.

BACKGROUND OF THE INVENTION

Seismocardiographic (SCG) devices and methods are known in the art. In general these devices use an accelerometer to monitor the patient's heart. In use, an accelerometer is placed on the surface of the patient to detect compression waves originating in the patient's heart. The compression waves received by the accelerometer are digitized and analyzed with a computer. These SCG devices may be used for cardiac monitoring and diagnostic purposes. In some instances the SCG is used as a replacement for electrocardiographic monitoring of heart rate. In the present invention the system is used to find time intervals between mitral valve opening (MO) and mitral valve closure (MC) times, as well as the opening time (AO) and closing times (AC) for the aortic valve. The time intervals may be used to compute classic measures of cardiac performance including the isovolumic contraction time and the left ventricular ejection time (LVET). At the present time such measures are made with echocardiography.

SUMMARY OF THE INVENTION

The purpose of the point picking process is to determine the aortic and mitral valve timing. The occurrence of AO, AC and MO, MC event is sought so that cardiac time interval measurements may be made.

The point pick methodology may be carried out with uni-directional i.e. single axis accelerometers, or with multiple axis accelerometers. A single accelerometer may be used or several accelerometers may be used.

In the parent case an illustrative example of a three sensor implementation is shown while this case focuses on a multiple axis sensor implementation. In essence a single sensor on the sterum looks for compression wave data such a carotid signal along the long axis of the patients body, and looks for apex motion signals along the short axis of the patient. These signal componts provide data that could also be sensed from separate carotid and apical sensors.

Therefore in one embodiment of the present system, several accelerometers are used, preferably three, in a several locations to accentuate the reception of different characteristics of the cardiac waveform. For example, one may use an acceleration sensor on the xyphoid process of the patient on the midline of the sternum as well as another accelerometer sensor at approximately the fourth intercostal space on the rib cage. This latter location places a sensor over the apex of the heart. In addition it is desirable to place a third sensor on the carotid artery on the patient's neck preferably above the bifurcation point where the common carotid divides into the external carotid and the internal carotid.

In operation, the SCG waveforms of the heart will usually be collected along with a conventional electrocardiographic (ECG) tracing. Certain mechanical events are "picked out" based upon a set of rules described in detail below. In one embodiment the ECG is an integral requirement of the point pick process since it provides a fiducial reference to permit averaging of the SCG waveforms.

In an alternate embodiment the SCG is evaluated for cardiac events without reference to the ECG. Either the SCG data is used in "w" form or it may be averaged using the carotid evidence of AO or AC as fiducial points for SCG averaging. This "SCG only" embodiment eliminates the need for a simultaneous ECG for SCG interpretation and may be particularly desirable where ECG recoding is difficult for example in a magnetic resonance imaging magnet.

In another embodiment of the invention one or more multiple axis accelerometers are used to extract vector information from the compression waves. In this embodiment the "xyphoid-carotid" signal may be from the long axis of the patient, while the "xyphoid-intercostal" signal may be derived from the short axis of the patient.

BRIEF DESCRIPTION OF THE DRAWINGS

Throughout the various figures identical reference numeral indicate identical structure, wherein;

FIG. 2 is a data sequence of simultaneously recorded waveforms from a patient in normal sinus rhythm (NSR) presented in several panels where;

FIG. 3 is data from a patient in normal sinus rhythm (NSR) in two panels where;

FIG. 4 is data along the Xyphoid to Carotid sensor on a patient in NSR in two panels where;

FIG. 5 is data from a patient in an atrial paced rhythm (AAI) in several panels where;

FIG. 6 is data from a patient in a ventricular paced rhythm (VVI) in several panels where;

DETAILED DESCRIPTION OF AN ILLUSTRATIVE EMBODIMENT

Overview

The objective of the method and device is to extract the "time" that certain cardiac events occur during the heart rhythm of a patient. In the heart a single heart contraction pumps blood and the sequence of mechanical events proceeds from mitral valve closure (MC) to aortic valve opening (AO). Next the aortic valve closes (AC) followed by mitral valve opening (MO). This sequence of cardiac valve actuation events results in the ejection of blood in to the aorta and the lungs. The opening and closing of valves give rise to the compression waves interpreted by the invention. These same mechanical events are caused by the contraction of the muscles in the heart which gives rise to an independent electrographic waveform (ECG) measured on the surface of the patient's body. Knowledge of the time intervals between these mechanical cardiac events and the electrographic counterpart events has substantial diagnostic value and any of several measures of cardiac performance may be computed from the time intervals.

Hardware Implementation

In the illustrative embodiment of the system, multiple channels of accelerometry derived from one or more sensors are used. Compression wave data may be detected from multiple spaced sensors, or derived from the response along defined axies from a single location. Multiple sensor, multiple axis implementations are contemplated as well. It is expected that certain optimization may be used to tailor the channels to their respective signals within the scope of the invention. The preferred location for a multiple axis accelerometer is on the xyphoid process or sterum area of the patient. The patient will typically be prone and inactive. However, alternate sites may be equivalent in terms of function. In this illustrative embodiment one multi-axis accelerometer resolves signal from a xyphoid-apex axis and from a xyphoid-carotid axis. The axes may be supplemented with a vertical Z axis component such that they are not solely planar signals or sensor responses.

Figure 1:
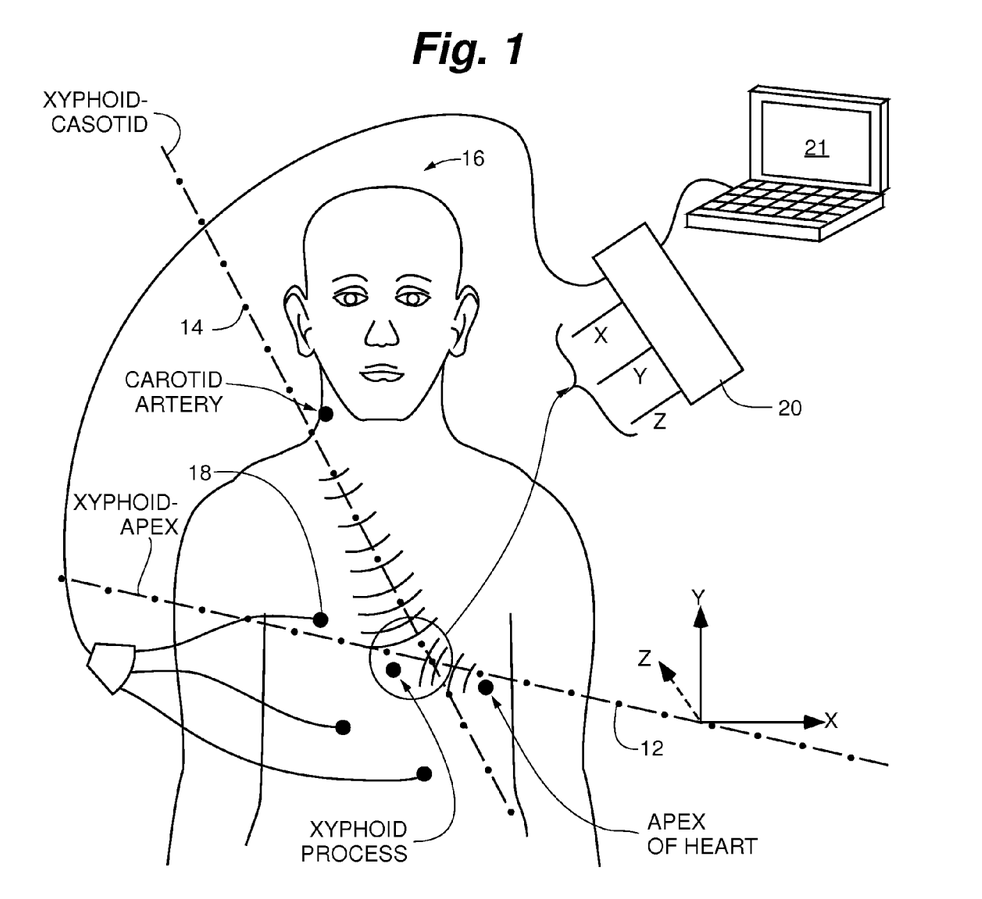
FIG. 1 is a schematic diagram of a multiaxis accelerometer system placed on a patient.

In use the sensor 10 is placed on the patient 16 to pick up different cardiac characteristics of a simultaneously recorded signals. That is, all the data is time stamped or aligned in time so that the point pick measurement process may move from one axis waveform to the other axis waveform. The waveform figures are displayed as panels to show this feature. As shown in FIG. 1, it is preferred, for example, to use a multiaxis acceleration sensor on the xyphoid process 10 of the patient on the midline of the sternum to record compression wave signal components from the X, Y and Z directions. Signal paths of interest are the X axis signal called "xyphoid to apex 12" and the Y axis signal called "xyphoid to carotid 14". Multiple electrode typified by electrode 18 are placed in a conventional "lead 12" pattern on the patient to pick up and record the ECG.

The accelerometers should have identical response on each axis and they may be piezoelectric devices with a frequency response for DC to 20,000 HZ generating approximately 1000 mv/G. The high impedance sensors generate signals that are delivered to the interface 20 via shielded cables. Commercially available multi axis accelerometer sensor may weigh as little as 20 grams or less which facilitates their placement on the body. The signal processing for the accelerometer signals of the three sensor axeses is similar and the signal processing and analog to digital conversion occurs in a companion interface 20. The invention has been implemented with the commonly available "Lab View" hardware platform manufactured by National Instruments Co. The SCG accelerometer signals are buffered and bandpass amplified with a flat filter having corner frequencies of approximately 0.3 Hz and 170 Hz. After filtration the signals are digitized with an A to D converter with a sampling rate of about 1K sps, and presented to the computer 21 which uses software to analyze the signals from the ECG and the SCG accelerometers. A user selectable interpretation recording is made of between about 3 to 15 seconds of data covering several beats. A moving 3-15 second window of data is recorded and is available for processing. Longer and shorter windows are operable.

Experimentation suggests that the system of the invention is quite tolerant of the signal processing methodology. Since implementation is readily carried out with "off the shelf" hardware the hardware implementation is not described in more detail.

SCG Point Pick Process

In most of the examples and during cardiac testing, the various SCG waveforms of the heart are collected along with a simultaneous conventional ECG tracing. The recordings are all taken simultaneously and the time relationship between the various waveforms or data sets is preserved. The SCG waveform is considered and processed as "wavelets" each wavelet is intended to encompass the time interval of a single heartbeat. Wavelets may be averaged or used individually (raw). A fiducial point for averaging SCG waveforms may be used to expand or contract the wavelet waveform to permit simple averaging of amplitude values. This fiducial point may be taken from the ECG channel where the electrocardiographic "R-wave" can be extracted from the ECG channel and used to scale and align the SCG waveforms. As an alternative the carotid SCG channel may be taken as indicative for certain events such as AO and AC. These mechanical events can be used scale and then average the SCG data. In general the averaging process expands or compresses the wavelets until they exhibit the same R-R interval. The averaging process is best achieved by manipulating the data by scaling the data so that it exhibits the same R-R interval and then making an arithmetic average of contiguous data sets at the same apparent heart rate. This forced rate ensures that mechanical motion events that are averaged at the same "time" in the cardiac cycle. It appears that the best performance is achieved when approximately 3-5 beats of data for each channel are taken and the data in each channel is averaged.

SCG Point Pick Process Schema Table

Figure 3A:
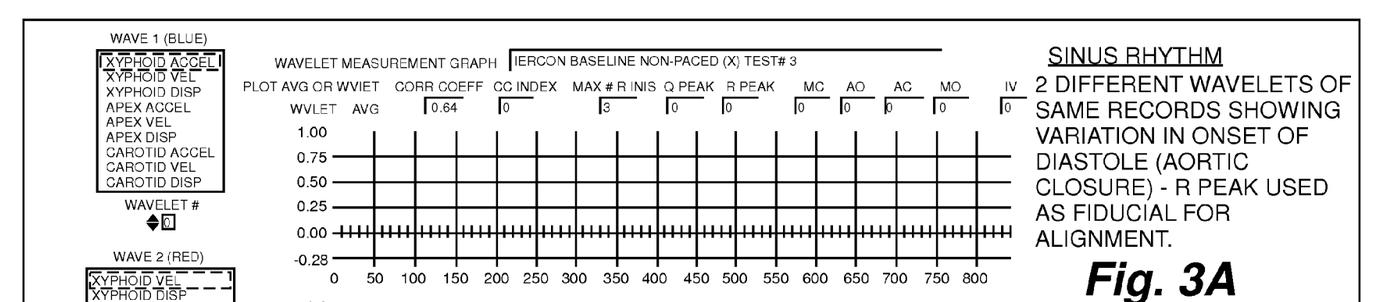
FIG. 3A is an event analysis presentation for a mechanical cardiac events of a patient's heart in NSR.
Figure 4A:
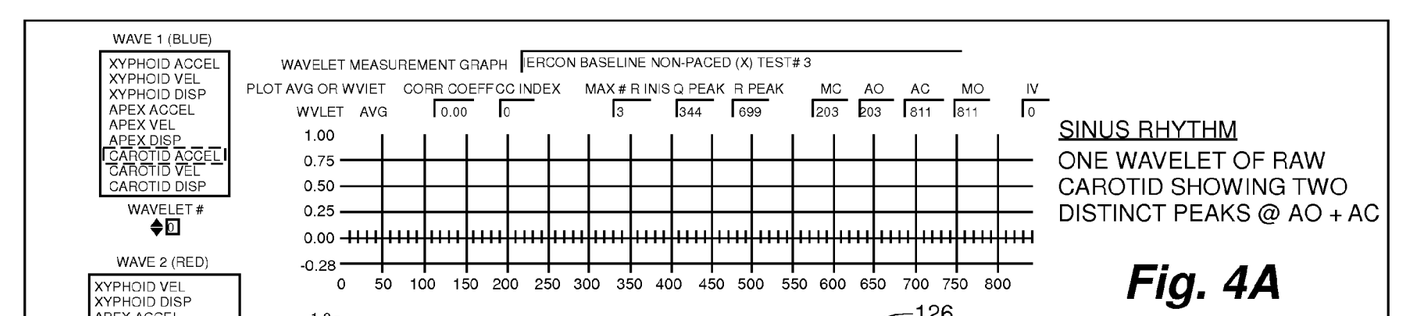
FIG. 4A is an event analysis presentation for mechanical cardiac events of a patient's heart in NSR.

This table represents the software process carried out by the computer 21 described in prose rather than a flow chart. This process is used to create the event analysis presentation seen as panel FIG. 3A and FIG. 4A, which can be viewed on a computer display screen. Wavelet or waveform averaging using the simultaneous ECG recording is described in more details in U.S. Pat. Nos. 4,989,611 and 5,159,932. The process described in the patent is similar channel for channel to the present implementation.

1. Point Pick Process with Simultaneous ECG

Figure 2A:
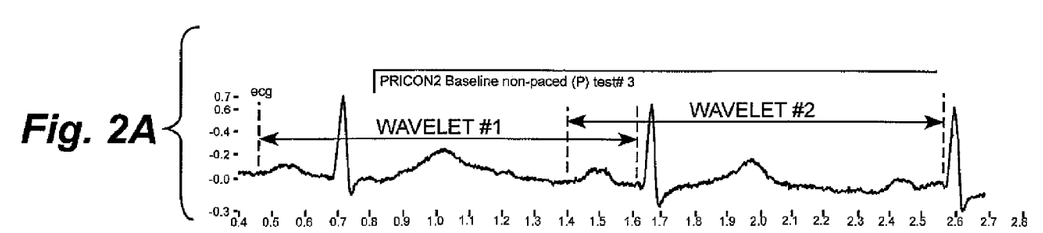
FIG. 2A is a surface ECG tracing.
Figure 2B:
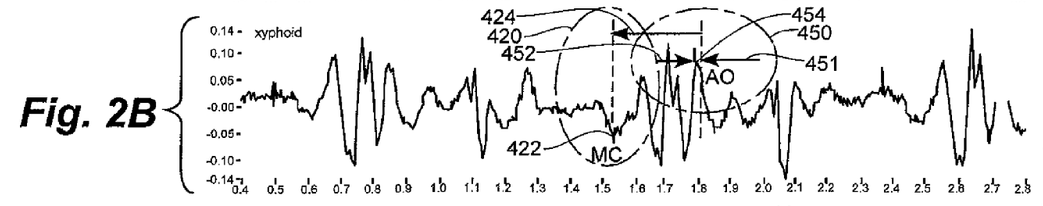
FIG. 2B is a predicted SCG tracing along the Z axis at Xyphoid sensor on the rib cage.
Figure 2C:
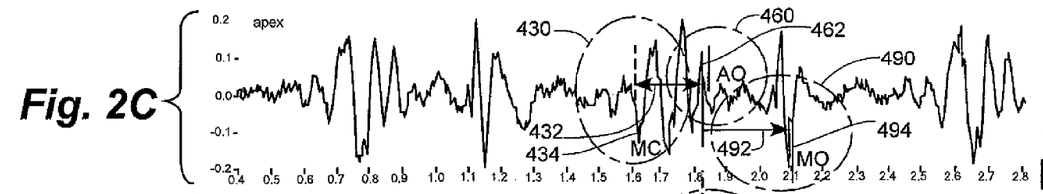
FIG. 2C is a predicted SCG tracing along the Xyphoid to Apex axis.
Figure 6A:
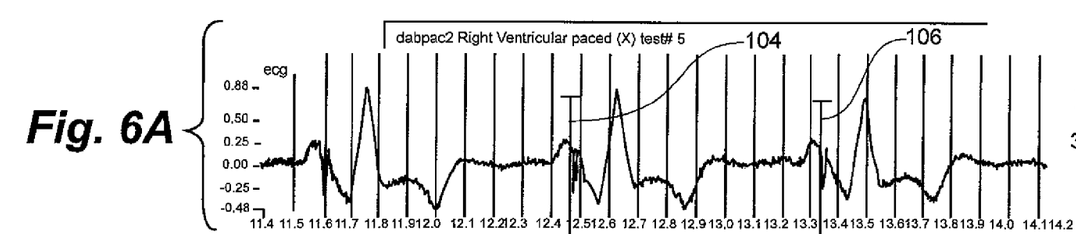
FIG. 6A is a surface ECG tracing.
Figure 6B:
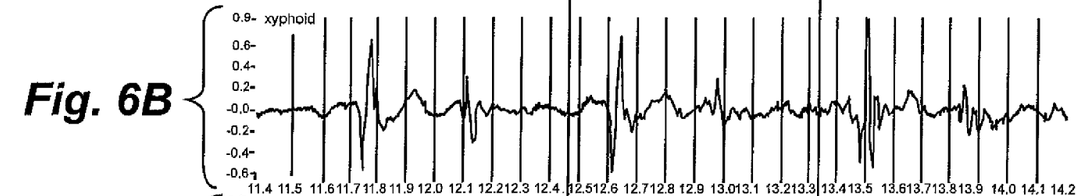
FIG. 6B is an SCG tracing from a xyphoid sensor on the rib cage.
Figure 6C:
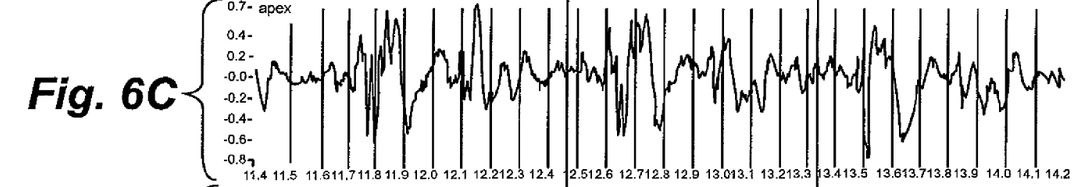
FIG. 6C is an SCG tracing from along the Xyphoid to Apex axis.
Figure 6D:
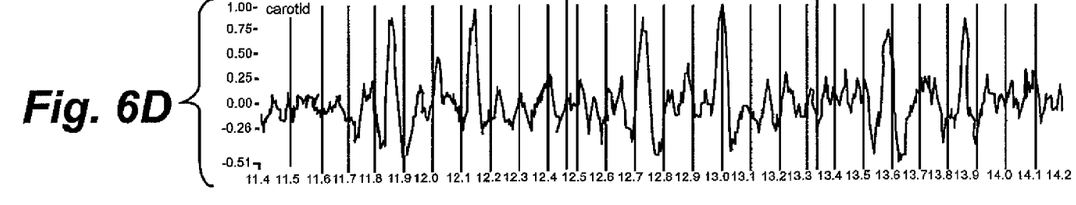
FIG. 6D is an SCG tracing from along the Xyphoid to Carotid axis.

A multiple channel ECG is collected from the patient to help with the evaluation of the SCG data. In general a lead "III" ECG waveform is sufficient and in this ECG channel there should be very distinct QRS complexes. Only a short interval of data needs to be collected with the present system. It has been determined that approximately 3 to 15 seconds of data is sufficient to carry out the invention. The electrocardiogram (ECG) is analyzed and conventional algorithms are used to determine the QRS onset as well as the peak of the R-wave. In FIG. 2A the magnitude and rise time of the waveform has resulted in the detection and declaration of event 100 and 102 as the "R-wave" in the respective complexes and the companion waveforms of FIG. 2. Rhythm analysis is provided to remove abnormal beats and in the instance of patients having a pacemaker, the pacemaker spike is used as the onset of the R-wave an example of this is seen in FIG. 6A where events 104 and event 106 represent the declaration of the onset of the "R-wave" in the waveforms of FIG. 6. In the ECG channel the system calculates the average standard deviation in medium R to R intervals of the heart to calculate the heart rate. The simultaneously recorded SCG data is evaluated by establishing an analysis window whose size is determined by the P to R interval and the R to R interval. The analysis window is the P to R to R interval of the average heartbeat. This window is applied to the ECG data as well as the simultaneously recorded SCG xyphoid, SCG apex and SCG carotid data. Once the R peaks are aligned a set of wavelets is created for each of the ECG channels. It is usually required to adjust the DC offset for the wavelet and every wavelet is integrated into a set of velocity wavelets. The velocity wavelets are used as a baseline and they are adjusted to remove noise. Next each velocity wavelet is integrated and a set of displacement wavelets are created. The displacement wavelets are baseline adjusted and any time dependant ramping behavior is removed as well.

Figure 3B:
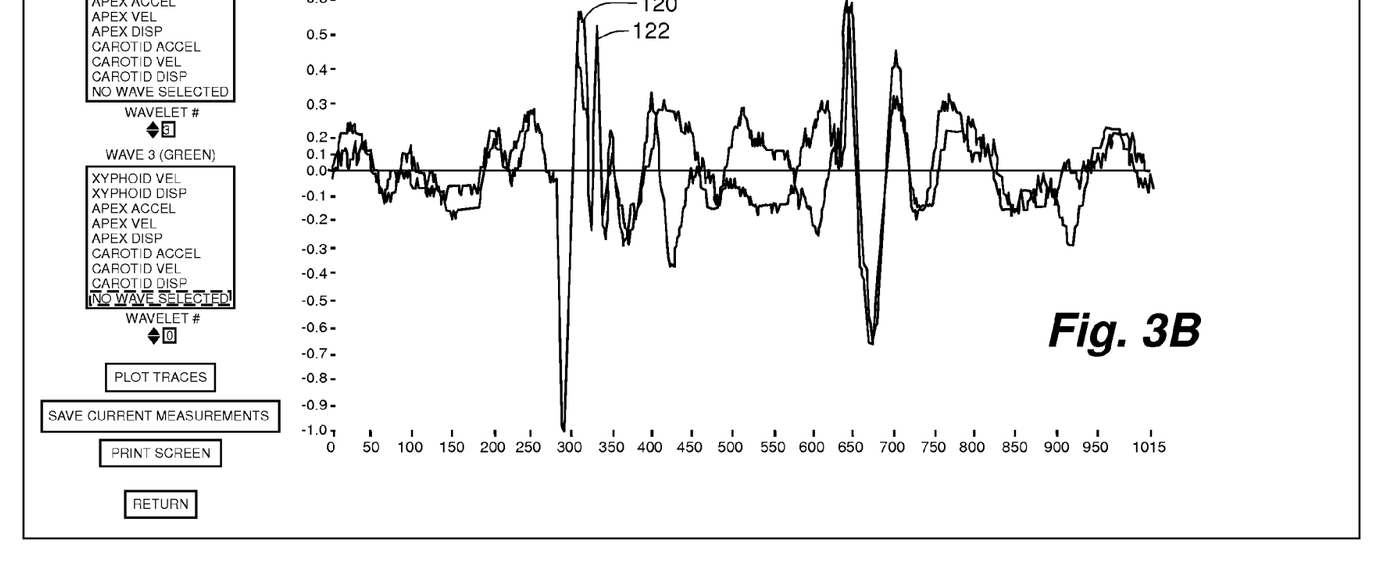
FIG. 3B is a tracing showing two SCG wavelets taken from a patient in NSR.

FIG. 3B shows two overlapping SCG waveforms from the carotid sensor on a patient in NSR. Wavelet 120 and wavelet 122 differ in detail even when aligned to the same "R-wave" as a fiducial reference. It has been found that averaging 3-5 beats greatly reduces the scatter in the event times shown in FIG. 3A. Although the wavelet disparity seen in FIG. 3B can be improved by averaging the beats around the electrographic R-wave another approach is available as well.

Figure 4B:
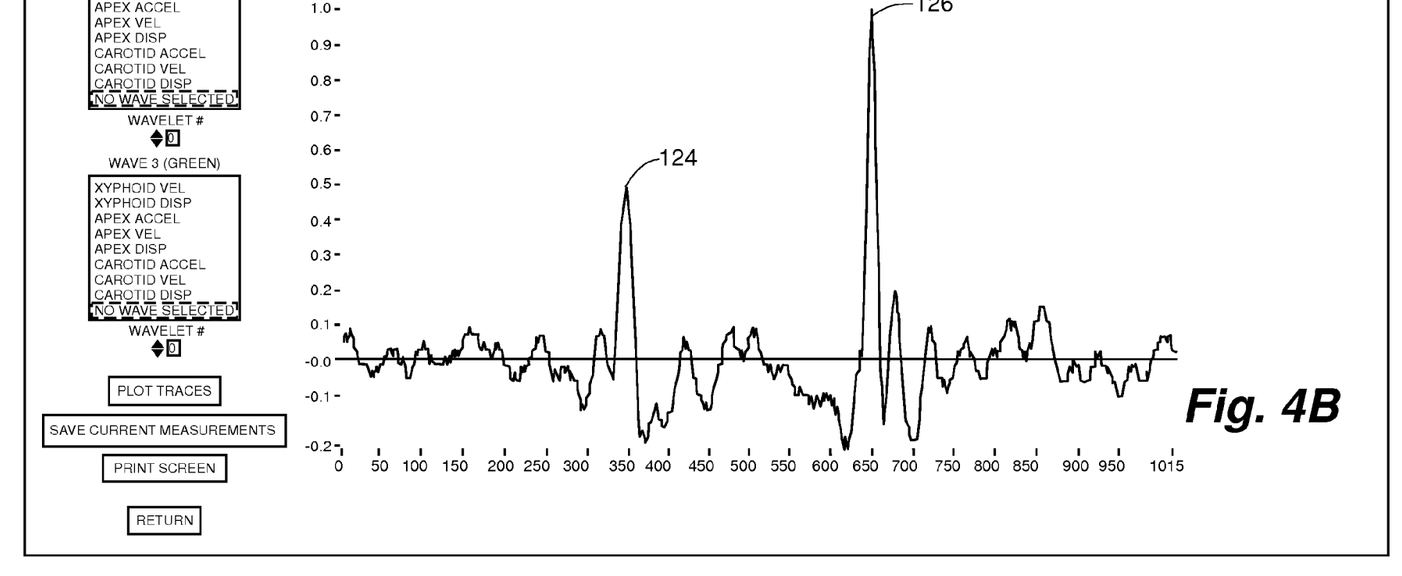
FIG. 4B is single carotid tracing of a patients heart in NSR.
Figures 5A, 5B:
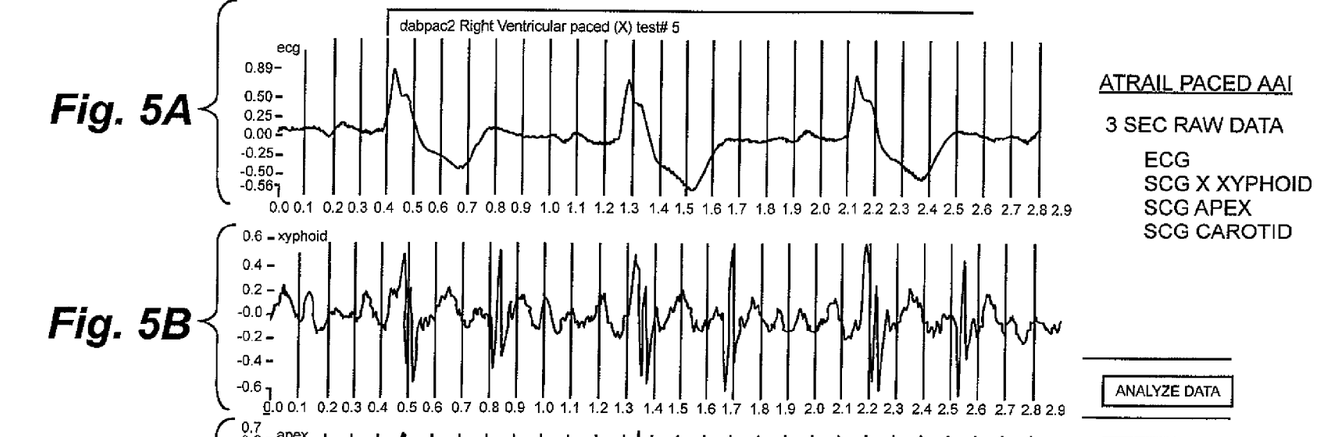
FIG. 5A is a surface ECG tracing.
FIG. 5B is an SCG tracing from the Xyphoid sensor on the rib cage.
Figures 5C, 5D:
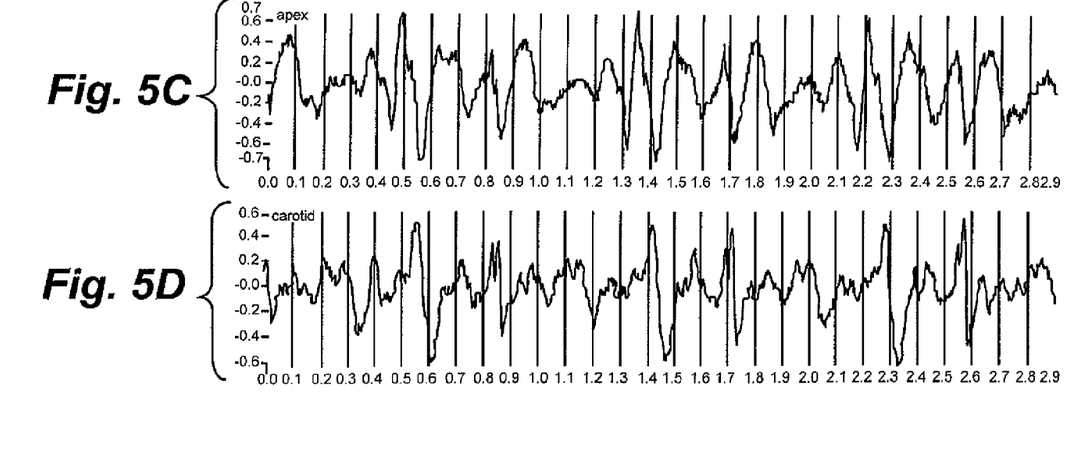
FIG. 5C is an SCG tracing from the Xyphoid to Apex axis.
FIG. 5D is an SCG tracing from the Xyphoid to Carotid axis.

The distinct inflections seen as 124 and peak 126 seen in FIG. 4B correspond to AO and AC mechanical events. These peaks are very distinct in the carotid waveforms presented in FIG. 4. In this instance the points may be selected using an "R-wave" like algorithm that looks at rise time dV/dT and Maximum value to declare the AO and AC events. One may use the AO and AC event to carry out averaging in the remaining SCG channels or they may be applied directly to the raw data in the companion waveforms. In this instance the remaining SCG point pick processes process maybe run in essentially real time without waveform averaging. With the SCG wavelets prepared the point picking process is applied. The process described in the patent is similar channel for channel to the present implementation.

The point picking process begins with the identification of aortic opening AO and proceeds sequentially to detect the MC, AC and MO events. With reference to the figures the process occurs according to the following rules and procedures.

Figure 2D:
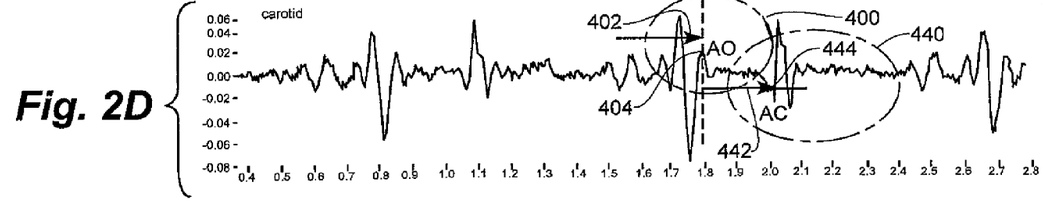
FIG. 2D is a predicted SCG tracing along the Xyphoid to Carotid axis.

AO process
Using the Average Carotid Acceleration Wavelet
Process 400 on FIG. 2D corresponds to:
   Identify the largest positive peak within 220 msec of the R peak see reference numeral 402;
    Mark this point as AO carotid, see reference numeral 404;
    If no positive peak is found, start search again at R peak and search ahead for largest negative peak. When found, search back for $1^{st}$ negative knee (concave down), mark this point AO carotid.
Using the Average Xyphoid Acceleration Wavelet
Process 450 on FIG. 2B corresponds to:
   Starting at AO carotid time, search back 60 msec for largest positive peak illustrated by arrows 451 and 452 which delimit the short time interval.
   Mark this point as AO xyphoid seen at reference numeral 454.
Using the Average Apex Acceleration Wavelet
Process 460 on FIG. 2C corresponds to:
   Starting at AO carotid time, search back 60 msec for largest negative peak    Mark this point as AO apex as shown by reference numeral 462.
If _AO xyphoid–AO apex_<=10 msec;
   Select AO apex as aortic valve opening AO.
If (AO xyphoid–AO apex)>=0 and _AO xyphoid–AO apex_>10 msec;
   Select AO xyphoid as pulmonic valve opening PO.
   Select AO apex as aortic valve opening AO.
If (AO xyphoid–AO apex)<0 and _AO xyphoid–AO apex_>10 msec;
   Select AO xyphoid as aortic opening AO.
MC process
Using the Average Xyphoid Acceleration Wavelet
Process 420 on FIG. 2B corresponds to:
   Start search at AO xyphoid time–10 msec and search back 85 msec for the largest negative peak, see reference numeral 424.
   Continue search back from this negative peak 30 msecs for $1^{st}$ negative knee.
   Mark this point MC xyphoid see reference numeral 422.
   If negative knee not found restart search at negative peak and search back for 45 msec to find $1^{st}$ positive peak.
   Mark this point MC xyphoid
Using the Average Apex Acceleration Wavelet
Process 430 on FIG. 2C corresponds to:
   Start search at AO apex time–10 msec and search back 100 msec for the largest negative peak, see reference numeral 432.
   Continue search back from this negative peak 30 msecs for $1^{st}$ negative knee.
   Mark this point MC apex as indicated by reference numeral 432.
   If negative knee not found restart search at negative peak back for 45 msec to find $1^{st}$ positive peak.
   Mark this point MC apex
If _MC xyphoid–MC apex_<=10 msec;
   Select earlier of MC apex or MC xyphoid as mitral valve closure MC.
If _MC xyphoid–MC apex_>10 msec and (MC xyphoid–MC apex)>0;
   Select MC xyphoid as tricuspid valve closure TC.
   Select MC apex as mitral valve closure MC.
If (MC xyphoid–MC apex)<0;
   Select MC apex as mitral valve closure MC.
AC process
Process 440 on FIG. 2D corresponds to:
Using the Average Carotid Acceleration Wavelet
Process 440 on FIG. 2D corresponds to:
   Starting at AO carotid time+200 msec, search ahead for 500 msec for largest positive peak see reference numeral 442.
   Mark this point as AC carotid see reference numeral 444.
Using the Average Xyphoid Acceleration Wavelet
Process 460 on FIG. 2B corresponds to:
   Start search AC carotid time–15 msec and search back 50 msec for the 1st negative peak
   Continue search back from this negative peak 20 msecs for $1^{st}$ negative knee.
   Mark this point AC xyphoid as shown by reference numeral 462.
   If negative knee not found restart search at negative peak and search back for 20 msec to find $1^{st}$ positive peak.
   Mark this point AC xyphoid
Using the Average Apex Acceleration Wavelet
Process 470 on FIG. 2C corresponds to:
   Start search at AC carotid time–15 msec and search back 50 msec for the 1st positive peak, Continue search back from this positive peak 20 msecs for 1$^{st}$ positive knee.
Mark this point AC apex
If positive knee not found restart search at positive peak and search back for 30 msec to find zero crossing.
Mark this point AC apex
If _AC xyphoid–AC apex_<=10 msec;
  Select earlier of AC apex or AC xyphoid as aortic valve closure AC.
If _AC xyphoid–AC apex_>10 msec and (AC apex–AC xyphoid)>0;
  Select AC xyphoid as tricuspid valve closure TC.
  Select AC apex as aortic valve closure AC.
If _AC xyphoid–AC apex_>10 msec and (AC apex–AC xyphoid)<0;
  Select AC apex as aortic valve closure AC.
MO process
Using the Average Xyphoid Velocity Wavelet
Process 480 on FIG. 2B corresponds to:
  Start search at AC carotid time+50 msec and search ahead 150 msec for the largest negative peak,
  Go to corresponding time point on the average xyphoid acceleration wavelet and search back 75 msec for the 1$^{st}$ positive knee,
  Mark this point MO xyphoid as indicated by reference numeral 482.
Using the Average Apex Velocity Wavelet
Process 490 on FIG. 2C corresponds to:
  Start search at AC carotid time+50 msec and search ahead 150 msec for the largest negative peak see reference numeral 492,
  Go to corresponding time point on the average apex acceleration wavelet and search back 75 msec for the 1$^{st}$ positive knee,
  Mark this point MO apex see reference numeral 494,
  Select the later of MO apex and MO xyphoid as mitral valve opening MO.
II. Point Pick Process without ECG
Point Pick process using AO peak identified in the SCG carotid trace for a fiducial point. The process of picking the AO peak in the carotid trace is essentially the same as QRS detector; setting threshold levels for noise and signal, setting refractory times for AO peak recurrence, and determining AO-AO interval. The AO peak will be used as fiducial marker for wave alignment and the wavelet window is equal to 0.35* avg AO-AO interval+AO-AO interval.
AO process
Using the average xyphoid acceleration wavelet
  Starting at AO carotid time, search back 60 msec for largest positive peak.
  Mark this point as AO xyphoid
Using the Average Apex Acceleration Wavelet
  Starting at AO carotid time, search back 60 msec for largest negative peak.
  Mark this point as AO apex
If _AO xyphoid–AO apex_<=10 msec;
  Select AO apex as aortic valve opening AO.
If (AO xyphoid–AO apex)>=0 and _AO xyphoid–AO apex_>10 msec;
  Select AO xyphoid as pulmonic valve opening PO.
  Select AO apex as aortic valve opening AO.
If (AO xyphoid–AO apex)<0 and _AO xyphoid–AO apex_>10 msec;
  Select AO xyphoid as aortic opening AO.

MC Process
Using the Average Xyphoid Acceleration Wavelet
  Start search at AO xyphoid time–10 msec and search back 85 msec for the largest negative peak
  Continue search back from this negative peak 30 msecs for 1$^{st}$ negative knee.
  Mark this point MC xyphoid
  If negative knee not found restart search at negative peak and search back for 45 msec to find 1$^{st}$ positive peak.
  Mark this point MC xyphoid
Using the Average Apex Acceleration Wavelet
  Start search at AO apex time–10 msec and search back 100 msec for the largest negative peak
  Continue search back from this negative peak 30 msecs for 1$^{st}$ negative knee.
  Mark this point MC apex
  If negative knee not found restart search at negative peak back for 45 msec to find 1$^{st}$ positive peak.
  Mark this point MC apex
If _MC xyphoid–MC apex_<=10 msec;
  Select earlier of MC apex or MC xyphoid as mitral valve closure MC.
If _MC xyphoid–MC apex_>10 msec and (MC xyphoid–MC apex)>0;
  Select MC xyphoid as tricuspid valve closure TC.
  Select MC apex as mitral valve closure MC.
If (MC xyphoid–MC apex)<0;
  Select MC apex as mitral valve closure MC.
AC Process
Using the Average Carotid Acceleration Wavelet
  Starting at AO carotid time+200 msec, search ahead for 500 msec for largest positive peak.
  Mark this point as AC carotid.
Using the Average Xyphoid Acceleration Wavelet
  Start search AC carotid time–15 msec and search back 50 msec for the 1st negative peak
  Continue search back from this negative peak 20 msecs for 1$^{st}$ negative knee.
  Mark this point AC xyphoid
  If negative knee not found restart search at negative peak and search back for 20 msec to find 1$^{st}$ positive peak.
  Mark this point AC xyphoid
Using the Average Apex Acceleration Wavelet
  Start search at AC carotid time–15 msec and search back 50 msec for the 1st positive peak
  Continue search back from this positive peak 20 msecs for 1$^{st}$ positive knee.
  Mark this point AC apex
  If positive knee not found restart search at positive peak and search back for 30 msec to find zero crossing.
  Mark this point AC apex
If _AC xyphoid–AC apex_<=10 msec;
  Select earlier of AC apex or AC xyphoid as aortic valve closure AC.
If _AC xyphoid–AC apex_>10 msec and (AC apex–AC xyphoid)>0;
  Select AC xyphoid as tricuspid valve closure TC.
  Select AC apex as aortic valve closure AC.
If _AC xyphoid–AC apex_>10 msec and (AC apex–AC xyphoid)<0; Select AC apex as aortic valve closure AC.
MO Process
Using the Average Xyphoid Velocity Wavelet
  Start search at AC carotid time+50 msec and search ahead 150 msec for the largest negative peak
  Go to corresponding time point on the average xyphoid acceleration wavelet and search back 75 msec for the 1$^{st}$ positive knee
  Mark this point MO xyphoid Using the Average Apex Velocity Wavelet
   Start search at AC carotid time+50 msec and search ahead 150 msec for the largest negative peak
   Go to corresponding time point on the average apex acceleration wavelet and search back 75 msec for the $1^{st}$ positive knee
   Mark this point MO apex
   Select the later of MO apex and MO xyphoid as mitral valve opening MO It should be apparent that many alternative modifications can be made to the invention without departing from the scope of the appended claims.

What is claimed is:

1. A device for monitoring and displaying cardiac function of a patient comprising:
   a.) at least one accelerometer sensor having multi-axis output, placed on the patient's body to collect vector accelerometer data along two axis selected from the set of xyphoid to apex of the heart axis, and xyphoid to carotid artery axis; said sensor generating signals in response to compression waves originating the heart along at least the two axes;
   b.) a signal processing system comprising multiple seisomocardiographic SCG channels coupled to said sensor for generating a SCG waveform along each axis, forming a carotid SCG channel waveform along one axis, and a xyphoid channel waveform along one axis, and a apex SCG channel waveform along one axis, and for recording and storing a segment of said SCG waveforms for analysis;
   c.) a module for extracting the time of mechanical events in the heart from said SCG waveform segment and for presenting the time of each such events to a system user on a display;
   d.) wherein said set of mechanical events is selected from the group comprising; mitral valve closing event MC, mitral valve opening event MO, aortic valve closing event AC, atrial valve opening AO;
   said device further comprising;
   e.) a set of electrocardiographic ECG electrodes placed on said patient's body for generating signals in response to electrical depolarization of originating the heart;
   f.) signal processing system coupled to said ECG electrodes for generating an ECG waveform, and for recording and storing a segment of said ECG waveform for analysis;
   g.) said atrial valve opening event AO module for carrying out a selection process in one SCG channel includes;
      forming an average carotid acceleration wavelet from said carotid SCG channel waveform;
      identify the R wave peak in the ECG channel;
      identify the largest positive peak in said SCG channel waveform within 220 msec of the R peak and mark this point as AO carotid, if no positive peak is found, start search again at R wave peak and search ahead for the largest negative peak, when found, search back for the first negative knee (concave down), and mark this point as AO carotid.

2. The device of claim 1 further comprising;
an AO module for carrying out a selection process in one SCG channel includes;
   forming an average xyphoid acceleration wavelet from said xyphoid SCG channel waveform;
   starting at AO carotid time, search back 60 msec for largest positive peak, and mark this point as AO xyphoid.

3. The device of claim 1 further comprising;
an AO module for carrying out a selection process in one SCG channel includes;
   forming an average apex acceleration wavelet from said apex SCG channel waveform;
   starting at AO carotid time, search back 60 msec for largest negative peak, and mark this point as AO apex;
   and if |AO xyphoid−AO apex|<=10 msec; then select AO apex as aortic valve opening AO;
   and if (AO xyphoid−AO apex)>=0 and |AO xyphoid−AO apex|>10 msec; select AO xyphoid as pulmonic valve opening PO, and select AO apex as aortic valve opening AO;
   and if (AO xyphoid−AO apex)<0 and |AO xyphoid−AO apex|>10 msec; then select AO xyphoid as aortic opening AO.

4. The device of claim 3 further comprising;
a MC module for carrying out a selection process in one SCG channel includes;
   forming an average xyphoid acceleration wavelet from said xyphoid SCG channel waveform;
   start search at AO xyphoid time−10 msec and search back 85 msec for the largest negative peak;
   continue search back from this negative peak 30 msecs for $1^{st}$ negative knee; and mark this point MC xyphoid; however,
   if a negative knee is not found restart search at negative peak and search back for 45 msec to find $1^{st}$ positive peak: and mark this point MC xyphoid.

5. The device of claim 3 further comprising;
a MC module for carrying out a selection process in one SCG channel includes;
   forming an average apex acceleration wavelet from said apex SCG channel waveform;
   start search at AO apex time−10 msec and search back 100 msec for the largest negative peak; and ,continue to search back from this negative peak 30 msecs for first negative knee; and mark this point MC apex; however if a negative knee is not found restart search at negative peak back for 45 msec to find first positive peak; then mark this point MC apex;
   if |MC xyphoid−MC apex|<=10 msec; then select earlier of MC apex or MC xyphoid as mitral valve closure MC; and,
   if |MC xyphoid−MC apex|>10 msec and (MC xyphoid−MC apex)>0; then,
   select MC xyphoid as tricuspid valve closure TC and select MC apex as mitral valve closure MC; however,
   if (MC xyphoid−MC apex)<0; then select MC apex as mitral valve closure MC.

6. The device of claim 1 further comprising;
an AC module for carrying out a selection process in one SCG channel includes;
   forming an average carotid acceleration wavelet from said carotid SCG channel waveform;
   starting at AO carotid time+200 msec, search ahead for 500 msec for largest positive peak; and,
   mark this point as AC carotid.

7. The device of claim 1 further comprising;
an AC module for carrying out a selection process in one SCG channel includes;
   forming an average xyphoid acceleration wavelet from said xyphoid SCG channel waveform;
   start search AC carotid time−15 msec and search back 50 msec for the 1st negative peak
   continue search back from this negative peak 20 msecs for $1^{st}$ negative knee mark this point AC xyphoid if negative knee not found restart search at negative peak and search back for 20 msec to find $1^{st}$ positive peak, then, mark this point AC xyphoid.

8. The device of claim 1 further comprising;

an AC module for carrying out a selection process in one SCG channel includes;

forming an average apex acceleration wavelet from said apex SCG channel waveform;

start search at AC carotid time−15 msec and search back 50 msec for the $1^{st}$ positive peak continue search back from this positive peak 20 msecs for $1^{st}$ positive knee, mark this point AC apex if positive knee not found restart search at positive peak and search back for 30 msec to find zero crossing, then, mark this point AC apex; and, if|AC xyphoid−AC apex|<=10 msec; then, select earlier of AC apex or AC xyphoid as aortic valve closure AC; and, if|AC xyphoid−AC apex|>10 msec and (AC apex−AC xyphoid)>0; and, select AC xyphoid as tricuspid valve closure TC, and, select AC apex as aortic valve closure AC; and, if|AC xyphoid−AC apex|>10 msec and (AC apex−AC xyphoid)<0; then, select AC apex as aortic valve closure AC.

9. The device of claim 1 further comprising;

an MO module for carrying out a selection process in one SCG channel includes;

forming an average xyphoid acceleration wavelet from said xyphoid SCG channel waveform;

start search at AC carotid time+50 msec and search ahead 150 msec for the largest negative peak, then, go to corresponding time point on the average xyphoid acceleration wavelet and search back 75 msec for the $1^{st}$ positive knee and, mark this point MO xyphoid.

10. The device of claim 1 further comprising;

a MO module for carrying out a selection process in one SCG channel includes;

forming an average apex acceleration wavelet from said apex SCG channel waveform;

start search at AC carotid time+50 msec and search ahead 150 msec for the largest negative peak;

go to corresponding time point on the average apex acceleration wavelet and search back 75 msec for the $1^{st}$ positive knee;

mark this point MO apex;

select the later of MO apex and MO xyphoid as mitral valve opening MO.

* * * * *